US00PP17715P2

(12) United States Plant Patent
Guillen

(10) Patent No.: US PP17,715 P2
(45) Date of Patent: May 8, 2007

(54) ***IMPATIENS* PLANT NAMED 'BALFAFUSIMP'**

(50) Latin Name: *Impatiens×hybrida*
Varietal Denomination: Balfafusimp

(75) Inventor: Mario Guillen, Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/296,833

(22) Filed: Dec. 7, 2005

(51) Int. Cl.
*A01H 5/00* (2006.01)

(52) U.S. Cl. ..... Plt./317

(58) Field of Classification Search ..... Plt./317
See application file for complete search history.

(56) References Cited

PUBLICATIONS

European Plant Breeders' Rights application No. 2005/2006 filed Oct. 25, 2005.

*Primary Examiner*—Anne Marie Grunberg
*Assistant Examiner*—S. B. McCormick-Ewoldt
(74) *Attorney, Agent, or Firm*—Audrey Charles

(57) ABSTRACT

A new and distinct cultivar of *Impatiens* plant named 'Balfafusimp' characterized by its fuchsia-colored flowers, dark green-colored foliage, and vigorous, trailing growth habit.

1 Drawing Sheet

Latin name of genus and species of plant claimed: *Impatiens×hybrida.*
Variety denomination: 'Balfafusimp'.

BACKGROUND OF THE INVENTION

The present invention relates to a new and distinct cultivar of *Impatiens* plant botanically known as *Impatiens×hybrida* and hereinafter referred to by the cultivar name 'Balfafusimp'.

The new cultivar originated in a controlled breeding program in Cartago, Costa Rica during March 2003. The objective of the breeding program was the development of *Impatiens* cultivars with numerous large flowers, attractive flower colors, and trailing, freely basal branching growth habit.

The female (seed) parent of the new cultivar was an unnamed proprietary *Impatiens×hybrida* breeding selection, not patented, characterized by its lilac-colored flowers and semi-prostrate growth habit. The male (pollen) parent of the new cultivar was a bulk of *Impatiens Hawkeri* pollen collected from the Java Series $F_1$ hybrid New Guinea *impatiens,* not patented, characterized by its medium vigor and a bushy well branched habit. The pollen was collected from several plants having a variety of flower colors and may have included orange, red, salmon, red and salmon bicolor, rose and lilac bicolor, lavender, cherry red, and white. The new *Impatiens* was discovered and selected by the inventor as a single flowering plant within the progeny of the above stated cross-pollination during April 2004 in a controlled environment at Cartago, Costa Rica.

Asexual reproduction of the new cultivar by terminal stem cuttings since April 2004 at Cartago, Costa Rica and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfafusimp' as a new and distinct cultivar of *Impatiens* plant:

1. Fuschia-colored flowers;
2. Dark green-colored foliage; and
3. Vigorous, trailing growth habit.

Plants of the new cultivar differ from plants of the female parent primarily in flower color and growth habit and from plants of the male parent primarily in growth habit.

Of the many commercially available *Impatiens* cultivars known to the inventor, the most similar in comparison to the new cultivar is 'Balfafusia', U.S. Plant Pat. No. 12,588. However, in side by side comparisons, plants of the new cultivar differ from plants of 'Balfafusia' in the following characteristics:

1. Plants of the new cultivar are taller than plants of 'Balfafusia';
2. Plants of the new cultivar have larger flowers as measured by flower diameter than plants of 'Balfafusia'; and
3. Plants of the new cultivar have more flowers per plant than plants of 'Balfafusia'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfafusimp'. The plants were grown in 10 cm pots for 10 weeks in a greenhouse at West Chicago, Ill.

DETAILED BOTANICAL DESCRIPTION

Figure 1:
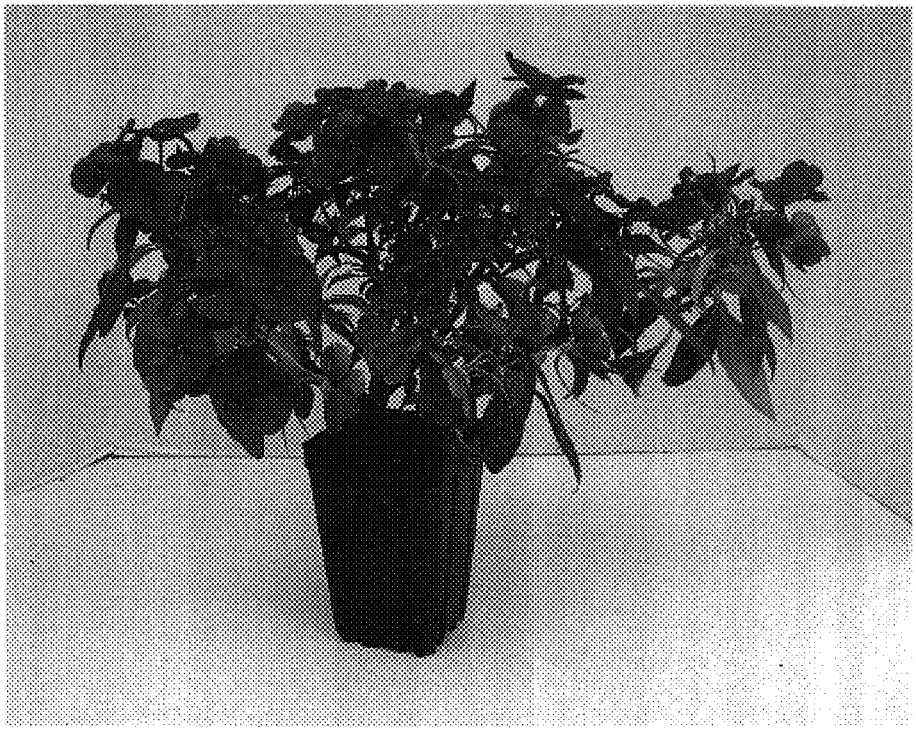
FIG. 1 illustrates a side view of the overall growth and flowering habit of 'Balfafusimp'.
Figure 2:
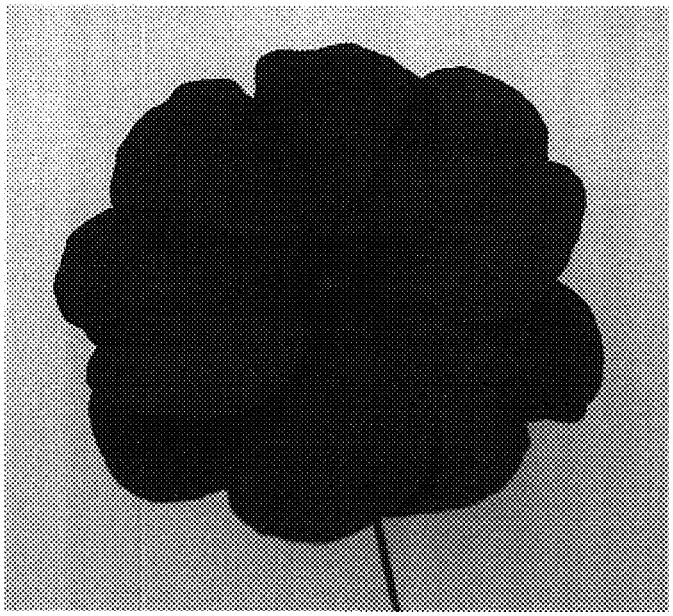
FIG. 2 illustrates a close-up view of an individual flower of 'Balfafusimp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Aug. 1, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 68° F. to 80° F. (20° C. to 26° C.) during the day and approximately 60° F. to 65° F. (15° C. to 18° C.) during the night. Greenhouse light levels of 4,000 to 7.000 footcandles were maintained during the day.

Botanical classification: *Impatiens×hybrida* cultivar Balfafusimp.

Parentage:

*Female parent.*—Proprietary unnamed *Impatiens×hybrida* breeding selection, not patented.

*Male parent.*—Java Series $F_1$ hybrid New Guinea *impatiens,* not patented.

Propagation:

*Type cutting.*—Terminal stem.

*Time to initiate roots.*—Approximately 7 to 8 days.

*Time to produce a rooted cutting.*—Approximately 21 to 28 days.

*Root description.*—Fine and fibrous.

*Rooting habit.*—Freely branching.

Plant description:

*Crop time.*—Approximately 6 to 8 weeks from a rooted cutting.

*Growth habit and general appearance.*—Vigorous, trailing.

*Size.*—Height from soil level to top of plant plane: Approximately 21.8 cm. Width: Approximately 49.6 cm.

*Branching habit.*—Freely basal branching. Approximately 4 branches per plant.

*Branch.*—Strength: Strong. Length: Approximately 19.8 cm. Diameter: Approximately 9.7 mm. Texture: Glabrous. Color: 144C with overlay of 187B. Internode length at center of branch: Approximately 3.7 cm.

*Foliage.*—Number of leaves per main branch: Approximately 16. Fragrance: None. Form: Simple. Arrangement: Opposite or in whorls of 3 to 5. Aspect: perpendicular to stem. Shape: Elliptic. Margin: Serrate, ciliate. Apex: Acuminate. Base: Attenuate. Venation pattern: Pinnate. Length of leaf at center of stem: Approximately 7.5 cm. Width of leaf at center of stem: Approximately 2.2 cm. Texture of upper and lower surfaces: Glabrous. Color of upper surface of mature foliage: 147A with venation of 144A with faint overlay of 183D. Color of lower surface of mature foliage: 147B with venation of 144A and faint overlay of 183D. Petiole length: Approximately 1.1 cm. Petiole diameter: Approximately 2.0 mm. Petiole texture: Glabrous. Petiole color: 145C.

Flowering description:

*Flowering habit.*—'Balfafusimp' is freely flowering under outdoor growing conditions with substantially continuous blooming from spring through autumn and year round in greenhouse environment.

*Time to first flower.*—Approximately 11.3 weeks from sticking of unrooted cutting.

*Lastingness of individual bloom.*—Approximately 6 to 7 days.

Flower description:

*Type.*—Single. Borne: Above foliage. Quantity of fully open flowers per plant at ten weeks: Approximately 40. Fragrance: None.

*Bud rate of opening.*—Generally takes 3 to 4 days for bud to progress from first color to fully open flower.

*Bud just before opening.*—Shape: Ovate. Quantity showing color at ten weeks: 5. Length: Approximately 1.4 cm. Width: Approximately 9.9 mm. Color: N78B.

*Corolla.*—Shape: Round. Slightly cupped when first open; petals become flattened with age. Diameter: Approximately 5.2 cm. Depth: Approximately 1.0 cm.

*Petals.*—Quantity: 5. Shape: Obovate. Aspect: Flat. Appearance: Iridescent. Margin: Entire. Apex: Emarginate. Base of upper petal: Truncate. Base of lateral and lower petals: Attenuate with each lateral petal fused with a lower petal at base. Texture: Glabrous. Length of upper petal: Approximately 2.0 cm. Width of upper petal: Approximately 2.7 cm. Length of lateral petal: Approximately 2.5 cm. Width of lateral petal: Approximately 2.5 cm. Length of lower petal: Approximately 2.8 cm. Width of lower petal: Approximately 2.7 cm. Color of upper surface of all petals when fully open: Darker than N74A with a small area of 71A at base. Color of lower surface of all petals when fully open: N74B with venation of N74A.

*Spur.*—Quantity: One per flower. Length: Approximately 4.9 cm. Diameter at tip: Approximately 0.8 mm. Diameter at base: Approximately 2.2 mm. Texture: Glabrous. Color: 185B with apex of 151C.

*Peduncle.*—Strength: Strong. Aspect: Erect to slightly acute angle to stem. Length: Approximately 4.0 cm. Diameter: Approximately 1.2 mm. Texture: Glabrous. Color: 145C with overlay of 187C.

*Calyx.*—Quantity of sepals per flower: 4. Upper sepal is fused to lower surface of upper petal. Apex: Acuminate. Texture of upper and lower surfaces: Glabrous. Shape of lateral sepal: Ovate. Length of lateral sepal: Approximately 1.3 cm. Width of lateral sepal: Approximately 5.8 mm. Color of lateral sepal: 157A with venation of 60B. Shape of lower sepal: Ovate. Length of lower sepal: Approximately 1.5 cm. Width of lower sepal: Approximately 1.0 cm. Color of lower sepal: N74C with 144B at apex.

*Reproductive organs.*—Androecium: Stamen quantity: 5, fused around pistil at apex. Anther shape: Hooded. Anther length: Approximately 2.0 mm. Anther color:

72B. Pollen amount: Moderate. Pollen color: 10C. Gynoecium: Pistil quantity: One per flower. Pistil length: Approximately 4.8 mm. Stigma shape: Five pointed star. Stigma length: Approximately 0.3 mm. Stigma color: Colorless, translucent. Style length: Approximately 1.0 mm. Style color: 145C. Ovary length: Approximately 3.5 mm. Ovary diameter: Approximately 1.4 mm. Ovary texture: Glabrous. Ovary color: N144D.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfafusimp', substantially as herein shown and described.

* * * * *